United States Patent [19]
Muchmore

[11] Patent Number: 5,215,918
[45] Date of Patent: Jun. 1, 1993

[54] ENANTIOMERIC ENRICHMENT OF (R,S)-3-QUINUCLIDINOL

[75] Inventor: David C. Muchmore, Springfield, Oreg.

[73] Assignee: Bend Research, Inc., Bend, Oreg.

[21] Appl. No.: 901,553

[22] Filed: Jun. 19, 1992

[51] Int. Cl.$^5$ .............................................. C12P 17/12
[52] U.S. Cl. .................................. 435/280; 435/836; 435/839
[58] Field of Search ........................ 435/280, 836, 839

[56] References Cited
PUBLICATIONS

Rehavi, M., Life Sci. 21(9):1293-1302 (1977).
Ringdahl, B., Acta Pharm. Suec. 16(4):281-3 (1979).

*Primary Examiner*—Douglas W. Robinson
*Assistant Examiner*—S. Saucier
*Attorney, Agent, or Firm*—Chernoff, Vilhauer, McClung & Stenzel

[57] ABSTRACT

A method for the enantiomeric enrichment of 3-quinuclidinol is disclosed, comprising acid anhydride esterification of the alcohol, followed by preferential enzymatic hydrolysis with a subtilisin protease.

5 Claims, 1 Drawing Sheet

ENANTIOMERIC ENRICHMENT OF (R,S)-3-QUINUCLIDINOL

BACKGROUND OF THE INVENTION

The esters of 3-quinuclidinol, the structure of which is shown below, contain the functional groups of acetylcholine and are known to possess muscarinic and antimuscarinic activity.

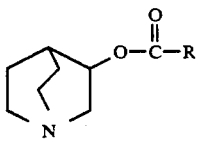

Biologically active quinuclidinol derivatives contain chiral centers, and so it is often highly desirable that they be in an enantiomerically-enriched or pure form, so as to improve specificity and reduce side effects. Consequently, the preparation of high optical purity quinuclidinols is of great interest.

The resolution of racemic mixtures of 3-quinuclidinol derivities has been reported. Rehavi et al., in 21 Life Sciences 1293 (1977), disclose the enzyme-catalyzed hydrolysis of (R)-3-quinuclidinol butyrate by butyrylcholine esterase from horse serum. However, the enantioselective hydrolysis of the (R)-ester to obtain R-alcohol was very slow (about 10 hours), resulted in low recovery and relatively low enantiomeric enrichment of the R-enantiomer, and required an enzyme which is very expensive.

There is still a need in the art for a simple, efficient, and inexpensive method of enantiomerically enriching chiral quinuclidinol and its derivatives. This need and others are met by the process of the present invention, which is summarized and described in detail below.

SUMMARY OF THE INVENTION

It has been found that racemic 3-quinuclidinol may be enantiomerically enriched by simply mixing the same with an acid anhydride, followed by selective enzymatic hydrolysis of the (S)-ester with a subtilisin protease and separating the desired enantiomer or its ester.

DETAILED DESCRIPTION OF THE PRESENT INVENTION

Figure 1:
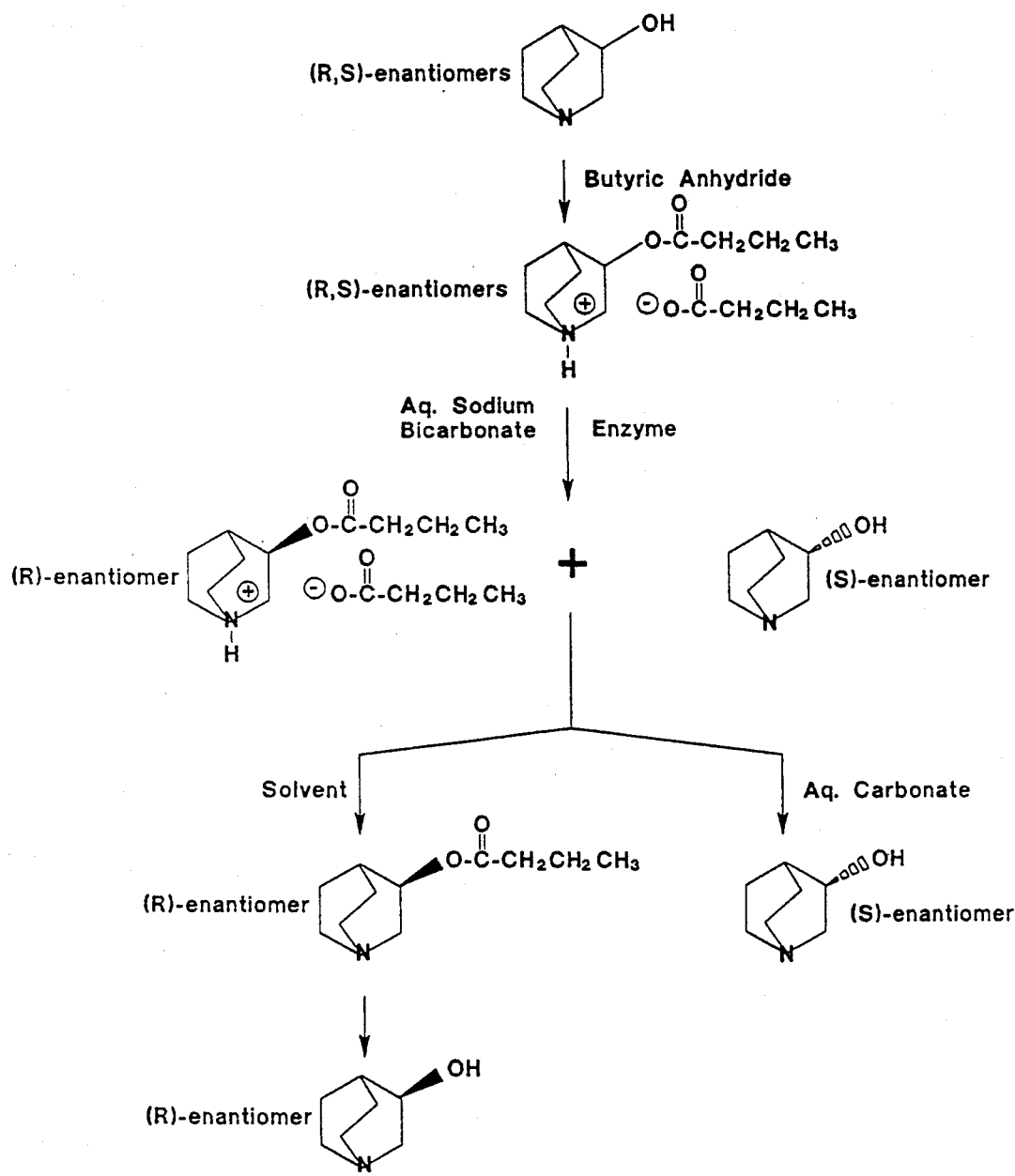
FIG. 1 is a schematic showing the reaction scheme of the method of the present invention.

According to the present invention, there is provided a method of enantiomerically enriching (R,S)-3-quinuclidinol comprising an acid anhydride acylation of the racemic mixture, followed by an enantioselective protease-catalyzed hydrolysis, and separation of the desired enantiomer or its ester. The catalyst is a subtilisin protease, and the acylating agent is a lower fatty acid anhydride selected from propionic, butyric, pentanoic and hexanoic acid anhydrides.

The term "enantiomeric enrichment" refers to the increase in the amount of one enantiomer as compared to the other. Enantiomeric enrichment may be effected by an increase or a decrease in the amount of one chiral form as compared to the other. A convenient method of expressing enantiomeric enrichment uses the concept of enantiomeric excess ("ee"), expressed by $$\% \ ee = \frac{[E1 - E2]}{[E1 + E2]} \times 100$$

wherein E1 is the amount of the first chiral form of the alcohol (or its ester) and E2 is amount of the second chiral form. Thus, if the initial ratio of the two chiral forms E1 and E2 is 50:50, as in a racemic mixture, and an enantiomeric enrichment is achieved that is sufficient to produce a final E1 to E2 ratio of 75:25, the ee with respect to the first chiral form would be 50%, calculated as $$\% \ ee = \frac{[75 - 25]}{[75 + 25]} \times 100 = 50$$

The reaction scheme shown in FIG. 1 illustrates the method when the acylating agent is butyric anhydride. A mixture of (R,S)-3-quinuclidinol is allowed to react with a slight excess of the acid anhydride to form the ester salt, which is then catalytically hydrolyzed in a slightly basic solution (5 wt. % aqueous bicarbonate). The hydrolysis is enantioselective for the (S)-enantiomer, which results in the enrichment of the ester and the (R)-enantiomer, and produces alcohol enriched in the (S)-enantiomer. The unreacted (R)-ester may be separated from the alcohol by raising the pH slightly, as by the addition of sodium carbonate to the solution to obtain a total carbonate concentration of 5 wt. %, which renders the (R)-ester (but not the (S)-quinuclidinol) extractable by a hydrocarbon solvent, such as hexane. Following extraction, the (R)-ester may be hydrolyzed by conventional methods to the (R)-alcohol. A particularly preferred method of hydrolysis comprises the use base and an alcohol, preferably sodium hydroxide and methanol. The (S)-alcohol may then be recovered from the reaction mixture by solvent extraction with a solvent having a high partition coefficient for quinuclidinol from water. Two exemplary and preferred such solvents are dichloromethane and chloroform.

Subtilisin proteases suitable for use in the hydrolysis of the (S)-quinuclidinyl ester include all proteases and genetic variants thereof which are produced by any member of the Bacillus genus. Exemplary sources of such proteases include the microorganisms *Bacillus subtilis*, *Bacillus amvloliouifaciens* and *Bacillus licheniformis*. Subtilisin Carlsberg is a preferred enzyme, as it is readily available from many sources.

In general terms, the process of the present invention uses an enzyme to selectively carry out a transformation that leaves the two enantiomers as two different chemical species that may then be separated by conventional chemical separation means. Specifically, the (R)-enantiomer remains as the ester while the (S)-enantiomer is transformed into the alcohol (S)-3-quinuclidinol. The extraction solvent is selected so that the solubility of the ester is high relative to the solubility of the alcohol. This is key to obtaining (R)-3-quinuclidinol of high enantiomeric excess, since any alcohol extracted along with the ester will be the wrong enantiomer. Hence, when the (R)-ester is hydrolyzed, this alcohol would be chemically indistinguishable from the (R)-quiniclidinol, and its presence would lower the enantiomeric excess of the (R)-alcohol.

If it is desired to isolate the (S)-quinuclidinol, it is important that all of the (R)-ester has been removed prior to the extraction of the (S)-alcohol, since it is difficult to find an extraction solvent in which the alcohol dissolves preferentially to the ester.

EXAMPLE

Twenty eight grams of racemic 3-quinuclidinol was dissolved in 35.0 g of butyric anhydride, and the mixture stirred for 16 hours, to form 62.2 g of the butyric acid salt of 3-quinuclidinyl butyrate. This ester salt was dissolved in 570 ml of 5 wt. % aqueous sodium bicarbonate solution, 2.8 ml of Alcalse 2.4 L (a preparation of subtilisin Carlsberg obtained from Novo Industri of Bagsvaerd, Denmark) was added, and the mixture was stirred at room temperature (23±2°) for 3.5 hours, at the end of which time no (S)-quinuclidnyl butyrate salt remained in the reactor.

The reaction mixture was cooled to 4° C., and 27 g of anhydrous sodium carbonate was added to bring the total carbonate concentration to 5 wt. %. The so-formed reaction mixture was then extracted with 6 400 ml portions of ice-cold hexane. The hexane extracts were combined, and the hexane was removed by distillation at reduced pressure. The residue was confirmed as the (R)-ester (R)-quinuclidinyl butyrate by the sign of its rotation.

An 18.7 g portion of the (R)-ester isolated in this fashion was dissolved in 15 ml of methanol and hydrolyzed with 2 ml of a 1M sodium hydroxide solution in methyl alcohol. The methanol was removed by distillation at reduced pressure, and the residue was dissolved in boiling toluene. The hot toluene solution was filtered and then allowed to cool to room temperature. The crystals that formed were collected and analyzed for yield, specific rotation, and enantiomeric excess (ee), all of which are reported in the table below.

| Compound | Yield | Specific Rotation | ee |
|---|---|---|---|
| quinuclidinyl butyrate | 100% | — | — |
| (R)-quinuclidinyl butyrate | 91% | 33° | — |
| (R)-quinuclidinol | 91% | −44.6° (46°*) | >95% |

*Literature value

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

What is claimed is:

1. A method of enentiomerically enriching chiral quinuclidinol comprising:
   (a) acylating a mixture of (R,S)-3-quinuclidinol with a lower fatty acid anhydride to form the corresponding (R,S)-lower fatty acid ester;
   (b) preferentially hydrolyzing the (S)-ester to (S)-3-quinuclidinol with a subtilisin protease as the catalyst; and
   (c) recovering (S)-3-quinuclidinol or the (R)-lower fatty acid ester of 3-quinuclidinol from the reaction mixture.

2. The method of the claim 1 wherein said fatty acid anhydride contains from 3 to 6 carbon atoms in the fatty acid.

3. The method of claim 2 wherein said fatty acid anhydride is butyric acid anhydride.

4. The method of claim 1 wherein the recovery of the (R)-lower fatty acid ester of 3-quinuclidinol is conducted by solvent extraction.

5. The method of claim 4 wherein, following recovery of said (R)-lower fatty acid ester, the same is hydrolyzed to the alcohol.

* * * * *

UNITED STATES PATENT AND TRADEMARK OFFICE
CERTIFICATE OF CORRECTION

PATENT NO. : 5,215,918
DATED : June 1, 1993
INVENTOR(S) : David C. Muchmore

It is certified that error appears in the above-identified patent and that said Letters Patent is hereby corrected as shown below:

Col. 2, Line 50:  delete "amvloliouifaciens" and insert
    -- amyloliquifaciens --

Signed and Sealed this

Twenty-fifth Day of January, 1994

Attest:

BRUCE LEHMAN

Attesting Officer

Commissioner of Patents and Trademarks